United States Patent
Baccelli et al.

(10) Patent No.: US 6,287,309 B1
(45) Date of Patent: Sep. 11, 2001

(54) SCREW AND PLATE SYSTEM FOR BACKBONE OSTEOSYNTHESIS

(75) Inventors: Christian Baccelli, Saint Medard d'Eyrans; Frédéric Conchy, Bordeaux; Patrick Henry, Quai Michelet, all of (FR)

(73) Assignee: DIMSO (Distribution Medicale du SudOuest) (FR)

( * ) Notice: Subject to any disclaimer, the term of this patent is extended or adjusted under 35 U.S.C. 154(b) by 0 days.

(21) Appl. No.: 09/509,242
(22) PCT Filed: Sep. 21, 1998
(86) PCT No.: PCT/FR98/02010
§ 371 Date: May 23, 2000
§ 102(e) Date: May 23, 2000
(87) PCT Pub. No.: WO99/15094
PCT Pub. Date: Apr. 1, 1999

(30) Foreign Application Priority Data

Sep. 23, 1997 (FR) .................................... 97 11811

(51) Int. Cl.⁷ ................................................ A61B 17/70
(52) U.S. Cl. .................................. 606/61; 606/69; 606/73
(58) Field of Search .................................. 606/61, 69, 70, 606/71, 72, 73

(56) References Cited

U.S. PATENT DOCUMENTS 5,728,127 * 3/1998 Asher et al. .......................... 606/61

* cited by examiner

*Primary Examiner*—David O. Reip
(74) *Attorney, Agent, or Firm*—Lerner, David, Littenberg, Krumholz & Mentlik, LLP

(57) ABSTRACT

A system for osteosynthesis of the spine. The system includes at least two pedicular screws and a linking plate for linking the screws together in an essentially rigid manner. Each screw has a bone anchoring threaded part, a non-circular section head, and a threaded end shank adapted to cooperate with a nut. The plate has at least one opening adapted to have the threaded end shank of a screw passed through it and be trapped between the screw head and the nut. A locking member is also provided for preventing relative angular movement between the heads of the screws and the linking plate. The locking member is adapted to be inserted between the plate and the screw head and includes a bore through which the threaded end shank of the screw passes, and further includes a first locking cooperation of shapes with the screw head and a second cooperation of shapes with the plate.

19 Claims, 4 Drawing Sheets

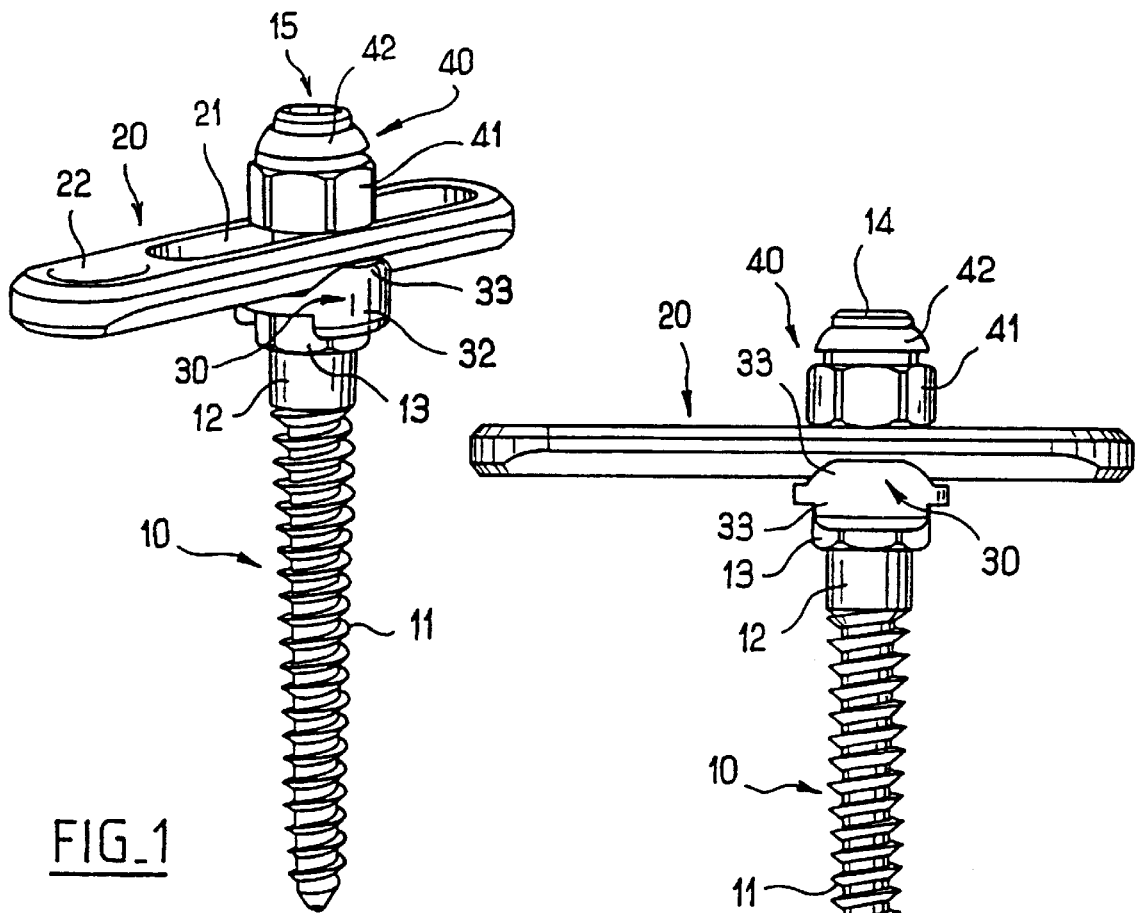
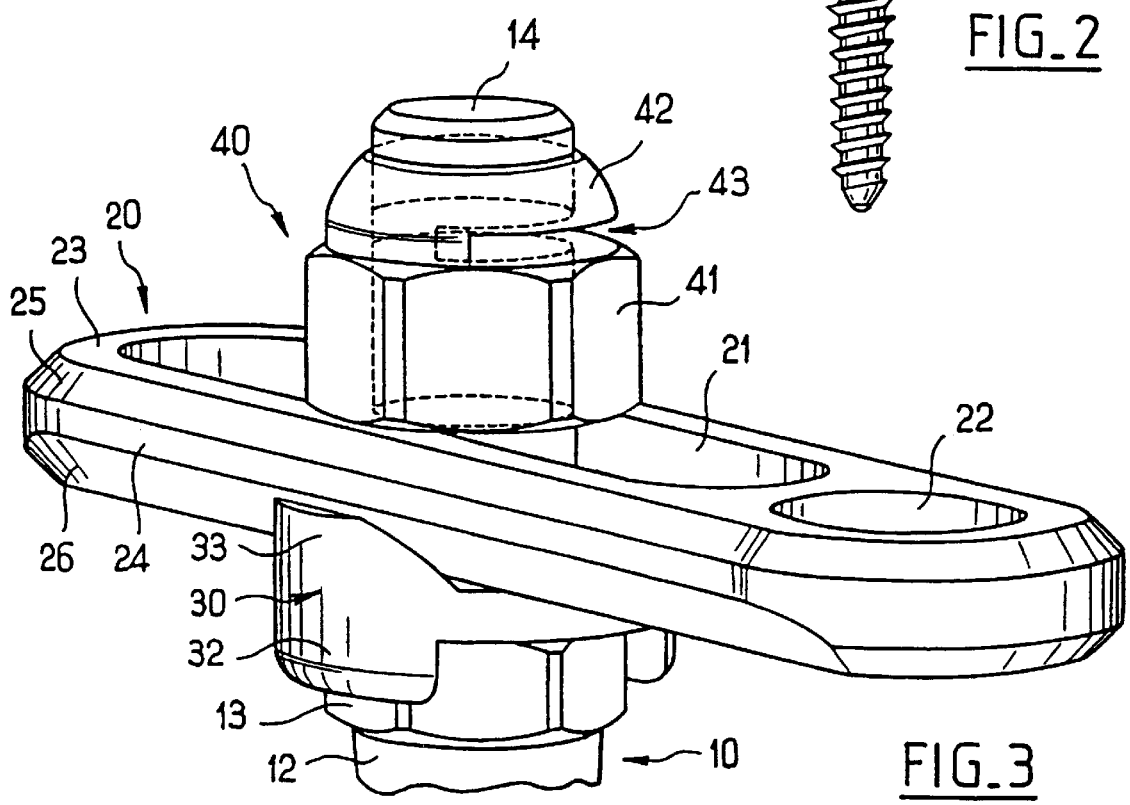

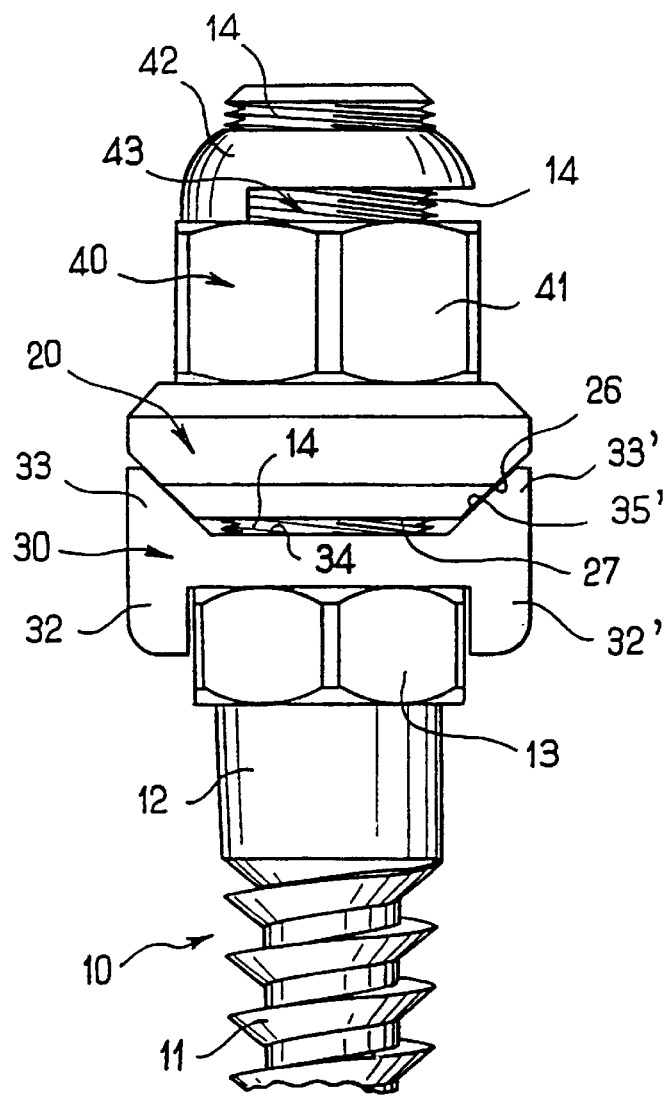
FIG_4
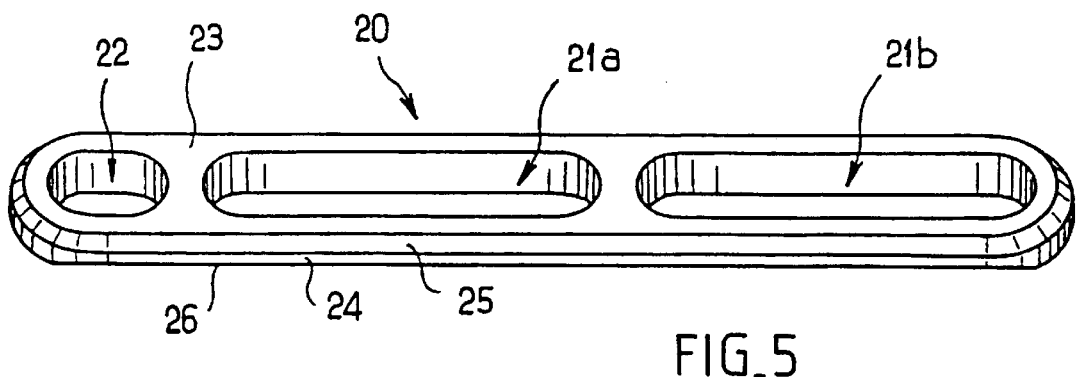
FIG_5

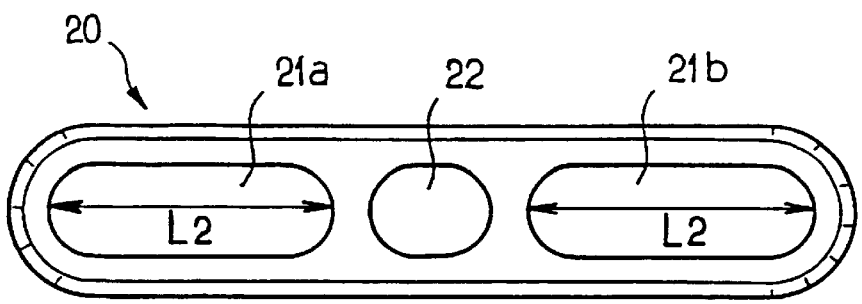
FIG_9
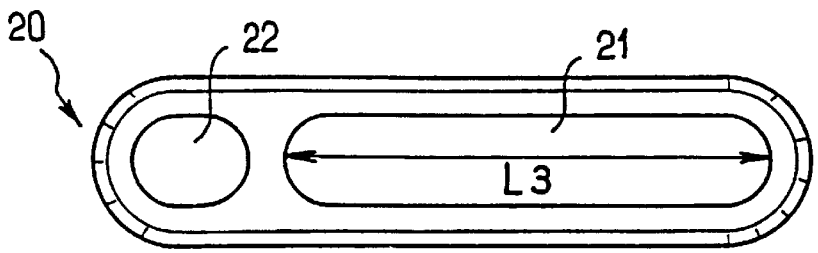
FIG_10
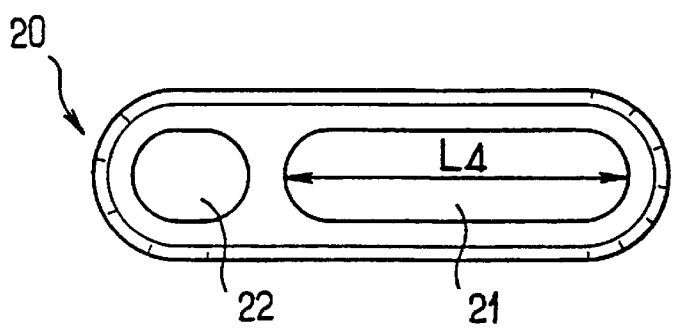
FIG_11
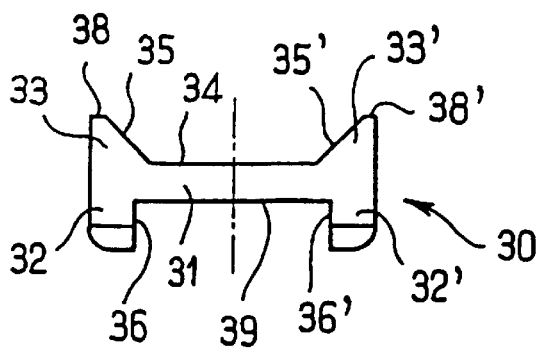
FIG_12
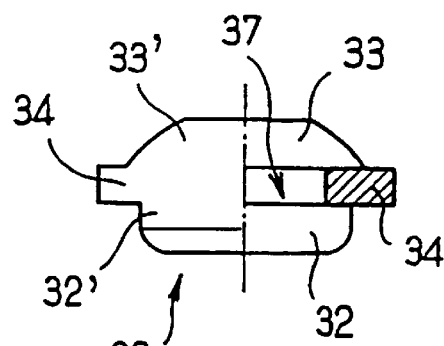
FIG_13
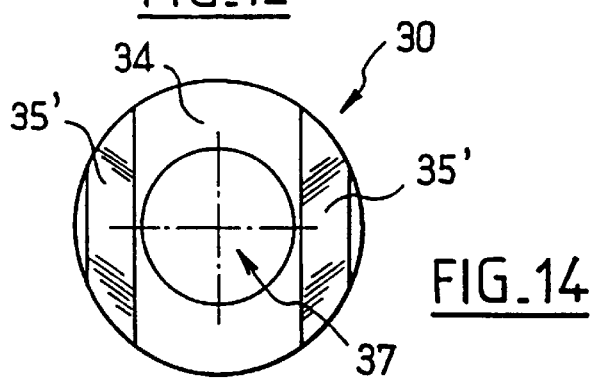
FIG_14

SCREW AND PLATE SYSTEM FOR BACKBONE OSTEOSYNTHESIS

BACKGROUND OF THE INVENTION

The present invention relates generally to systems of the "plate" type for osteosynthesis of the spine.

Systems of this kind are known in the art and include at least two pedicular screws anchored in adjacent vertebrae to be treated and a connecting plate designed to connect the screwheads together in a rigid manner.

EP-A-0 441 084 in particular discloses a system of this kind in which each pedicular screw has a hexagonal section part for inserting the screw into the bone and on top of which is a threaded shank.

The plate has a plurality of oblong openings through which the various threaded shanks can be inserted and an open groove on its bottom face to prevent rotation of the hexagonal part of each pedicular screw, in order to prevent it coming loose.

Each pedicular screw is associated with a stirrup through which the threaded shank of the screw also passes and which straddles the top of the plate; finally, a nut is screwed onto the threaded shank to trap and immobilize the plate with the stirrup on top of it, between it and the hexagonal part of the screw.

Complementary raised patterns are provided on the top face of the plate and on the bottom face of the stirrup to prevent longitudinal sliding of the plate relative to the screw.

Although it is generally satisfactory, this fixing system nevertheless has certain drawbacks.

The raised patterns have to be provided to prevent sliding because the plate and the stirrup cooperate only via two plane faces in compression and so their absence would lead to the risk of entirely unacceptable relative movement of the vertebrae.

The machining required by these raised patterns significantly increases the unit cost of the plates and the stirrups.

Also, the raised patterns can impede fine adjustment of the system in that they allow only a particular number of discrete mutual positions of the plate and the stirrup, i.e. a particular number of discrete distances between the screws; moreover, if the nut is overtightened before the final tightening, mutual sliding of the plate and the stirrup during adjustments may be impeded.

Finally, the above prior art system requires the various stirrups to be attached to the top of the plate, before screwing on the nuts, which is irksome and entails the risk of incorrect positioning of the stirrups before tightening.

SUMMARY OF THE INVENTION

The present invention aims to alleviate the above drawbacks and to propose a plate-type connecting system in which the various components require much simpler machining, but which still offers excellent stability.

Another object of the invention is to propose a system which is simpler to fit because it avoids the irksome and unstable fitting of the stirrups before fitting the nuts.

A further object of the present invention is to propose a system which has some degree of elastic deformability, for improved distribution of the stresses between the various vertebrae.

The present invention therefore proposes a system for osteosynthesis of the spine, including at least two pedicular screws and a connecting plate adapted to connect the screws together in an essentially rigid manner, each screw having a bone anchor threaded part and a non-circular section head, as well as a threaded end shank adapted to cooperate with a nut, the plate having at least one opening adapted to have the threaded end shank of a screw passed through it and to be trapped between said non-circular section head and said nut, locking means being provided for preventing relative angular movement between the head of each particular screw and the plate, characterized in that the angular locking means include an attached member between said plate and said head of the particular screw and through which the threaded end shank of the latter passes, this member providing a first locking cooperation of shapes with said head and a second locking cooperation of shapes with said plate.

Preferred, but non-limiting, aspects of the system according to the invention are:

the first locking cooperation of shapes is a straddling of said non-circular section head by said attached member from above;

said attached member has two lateral legs delimiting between them a channel with straight edges whose width is slightly greater than the distance between two parallel flats of the head of said pedicular screw;

the second locking cooperation of shapes is a straddling of said plate by said attached member from below;

said attached member has two lateral columns defining between them a channel with oblique raised edges and said plate has lateral bevels adapted to bear against said oblique edges;

said plate bears only on said bevels of said attached member;

said attached member has a core which is generally disk-shaped with a central hole through it through which the threaded end shank of the pedicular screw can be passed;

the width of the attached member is substantially equal to that of the plate;

the system includes a set of pedicular screws and a set of plates which have different configurations of holes, with one slightly oblong hole of constant geometry and one or more elongate holes of different lengths;

the nut bears directly against the top face of the plate.

Other aspects, aims and advantages of the present invention will become more apparent on reading the following detailed description of one preferred embodiment of the invention, which is given by way of example only and with reference to the accompanying drawings, in which:

BRIEF DESCRIPTION OF THE DRAWINGS

FIG. 1 is a general perspective view of a spinal implant according to the invention, FIG. 2 is a side elevation view of the implant, FIG. 3 is another perspective view of the implant, to a larger scale, FIG. 4 is an end elevation view of the implant, FIG. 5 is a perspective view of a plate used in the implant, FIG. 12 is a front elevation view of a connecting and locking member of the implant, FIG. 13 is a side view of the member shown in FIG. 12, and FIG. 14 is a plan view of the member shown in FIGS. 12 and 13.

DETAILED DESCRIPTION OF THE INVENTION

Figure 7:
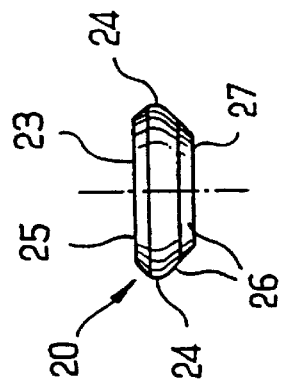
FIG. 7 is an end elevation view of the plate shown in FIG. 6.
Figure 6:
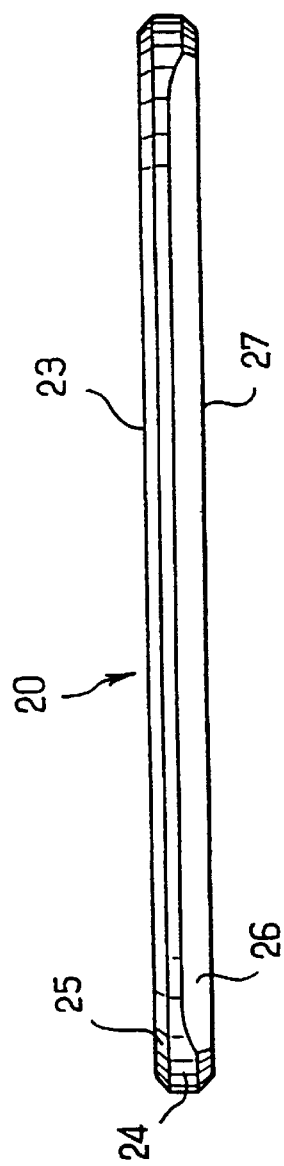
FIG. 6 is a side elevation view of another version of the plate.

The drawings show a "plate"-type implant for osteosynthesis of the spine, the principle of which entails anchoring a series of pedicular screws 10 into adjacent vertebrae and connecting the screws 10 together in a rigid manner using a perforated plate.

For clarity, FIGS. 1 to 4 show the cooperation of the plate with only one of the screws.

Each screw 10 conventionally has, from one end to the other, a threaded part 11 to enable it to be anchored in a vertebra, a neck 12, a hexagonal section head 13 to enable the screw to be screwed into a vertebra using a wrench, and finally a threaded cylindrical end part 14 in which the thread is of constant diameter and constant pitch. The top of the threaded part 14 can incorporate a hexagonal imprint 15 (FIG. 1) enabling the screw 10 to be screwed into a vertebra from above using a hex key.

The connecting plate 20 is of generally flat and rounded shape with semicircular ends. It is delimited by a top face 23, a bottom face 27, a side face 24, a first 45° bevel 25 at the transition between the top face 23 and the side face 24 and a second 45° bevel 26 at the transition between the bottom face 27 and the side face 24.

Note that the bottom bevel 26 is wider along the flanks of the plate than at its ends.

A series of holes oriented in the longitudinal direction of the plate 20 for assembling the plate and the pedicular screws pass through the plate in the direction of its thickness. There are typically one short oblong hole 22 and one or more longer oblong holes 21, various arrangements of the holes being described in more detail below.

The system also includes an intermediate member 30 and a nut 40 associated with each screw 10.

The width of the intermediate member 30 is substantially equal to that of the plate 20 and this member includes a generally disk-shaped central body 31 through which passes a central hole 37 whose diameter is slightly greater than the overall diameter of the threaded shank 14 of the screw 10.

Two diametrally opposite regions of the body 31 include downwardly extending legs 32, 32' whose outside surfaces mate with the circular contour of the body 31 and whose inside surfaces have two straight and parallel faces 36, 36' facing each other. The distance between these faces is slightly greater than the distance between two opposite flats of the hexagonal head 13 of the screw 10. The faces 36, 36' delimit a plane face 39 constituting the bottom face of the body 31 of the member 30.

The outside faces of the legs 32, 32' are slightly rounded at the bottom to avoid potentially traumatizing sharp edges.

Upwardly extending columns 33, 33' in the same diametrally opposite regions of the body 31 of the member 30 have outside surfaces which mate with the circular contour of the body.

The columns have respective inside faces 35 and 35' beveled at 45° which delimit between them a plane bottom area 34 constituting the top surface of the body 31.

FIG. 12 in particular shows flats 38 parallel to the face 34 which provide a transition between the top ends of the faces 35, 35' and the top ends of the outside edges of the column to avoid a potentially traumatizing very sharp edge.

It is important to note here that the width of the bottom 34 of the member is slightly less than the width between the bevels of the inside face 27 of the plate 20, for reasons explained below.

Finally, the nut 40 is in itself of a conventional type. It has a hexagonal body 41 with six flats for tightening it, on top of which is a domed part 42 separated from said body 41 by a transverse slot 43.

An axial thread passes through the body 41 and the domed part 42 and slight plastic deformation of the nut by compressing it at the level of the slot 43 enables slight misalignment of the two parts of the thread on respective opposite sides of the slot 43, so that the nut is of the self-locking kind.

The implant as described above is fitted in the following manner.

A number of pedicular screws 10 are inserted into adjacent vertebrae, after which each screw first receives a member 30 positioned so that the faces 36, 36' and 39 of the head 13 of the screw fit in the channel defined on the bottom of the member 30 and the top of said head 13 bears against said face 39.

The members 30 are also oriented so that the axes of the top channels defined between their faces 34, 35 and 35' are essentially aligned.

A plate 20 with appropriate geometry is then fitted so that the threaded shanks 14 of the screws are inserted in the holes 21 or 22 through the plate and the base of said plate rests in the respective top channel of each member, which forms a cradle.

The plate is self-centered on the respective member 30 during this operation by cooperation between the lateral parts of the bevels 26 of the plate and the 45° faces 35 and 35' of each member 30.

The nuts 40 are then screwed onto the threaded shanks 14 of the screws 10 to press the plate 20 into its respective cradle.

Because the bottom face 27 of the plate is wider than the bottom 34 of the cradle the plate 20 is in contact with only the 45° faces of the member 30, namely the bevels 26 and the beveled faces 35, 35', even after the nut is completely tightened, which is particularly advantageous. Thus FIGS. 2 and 4 in particular show that, after tightening, a small gap, typically from 0.5 mm to 2 mm wide, remains between the respective faces 27 and 34 of the plate 20 and the member 30.

This feature ensures that the plate 20 and each member 30 cooperate along oblique lines of force, which causes slight elastic deformation of the materials and therefore high reaction forces at the bearing faces.

This being so, there is sufficient friction between the bearing faces to ensure that locking of the assembly is totally stable and to avoid the need to use raised patterns, notches or other means of preventing unwanted sliding.

The operating technique required of the surgeon is facilitated by the fact that, after the plate 20 is fitted, the member 30 is trapped between it and the respective heads 13 of the screws 10.

Other features of the invention will now be described, relating in particular to the plate 20.

FIGS. 5, 8, 9, 10 and 11 show different arrangements of the oblong holes 21 and 22.

Figure 8:
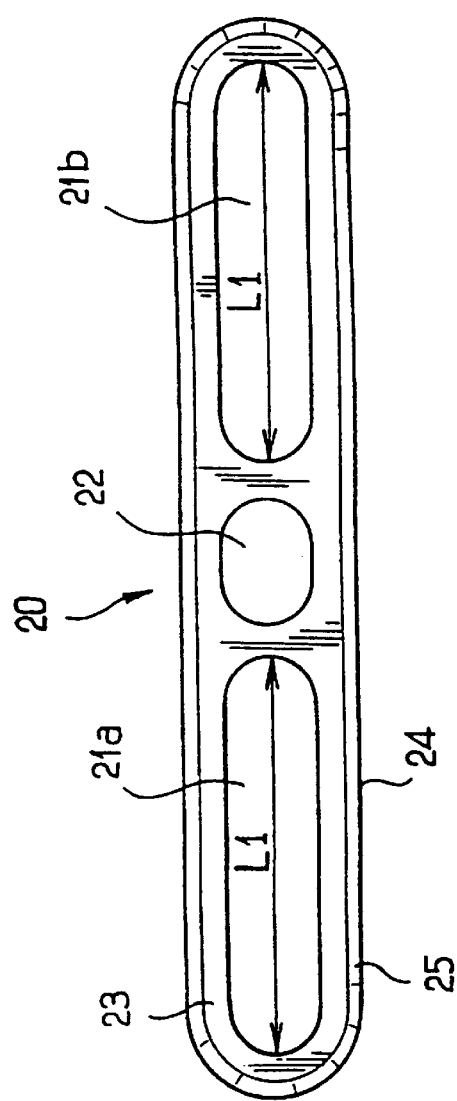
FIG. 8 is a plan view of the plate shown in FIGS. 6 and 7, FIGS. 9 to 11 are plan views of three other versions of the plate.

FIGS. 8 and 9 show a short hole 22 between two long holes 21, and versions can be proposed with different lengths of the long holes (L1 in FIG. 8 and L2, less than L1, in FIG. 9).

The short hole 22 can also be at one end of the plate, and associated with one long hole 21 (FIGS. 10 and 11) or two long holes 21a, 21b (FIG. 5).

A plate with a short hole 22 at one end of the area of the spinal column to be treated prevents the implant system projecting undesirably toward the adjacent sound area.

FIGS. 10 and 11 show two long holes 21 of different lengths, respectively L3 and L4.

In practice, the surgeon is offered a set of plates which all have the same cross section and the various arrangement referred to above or other arrangements.

The dimensions of the plates can be chosen so that there is some capacity for elastic deformation between two particular screws, which improves the distribution of stresses between the various vertebrae.

If the plates are made from a standard biocompatible titanium alloy, the branches of the plate flanking each hole 21 or 22 typically have the particular shape described above and a cross section area that is preferably from 6 to 11 mm$^2$ and more preferably from 7.5 to 9.5 mm$^2$.

Of course, the present invention is in no way limited to the embodiments described above and shown in the drawings, which the skilled person will know how to modify or vary in any way conforming to the spirit to the invention.

What is claimed is:

1. System for osteosynthesis of the spine, including at least two pedicular screws for insertion into vertebrae and a connecting plate adapted to connect the screws together in an essentially rigid manner, each screw having a bone anchor threaded part and a non-circular section head, as well as a threaded end shank adapted to cooperate with a nut, the plate having at least one opening adapted to have the threaded end shank of a screw passed through it and to be trapped between said head and said nut, a locking means being provided for preventing relative angular movement between the head of each pedicular screw and the plate, the locking means including a member added between said plate and said head of the pedicular screw and through which the threaded end shank of the latter passes, wherein the member provides a first locking cooperation of shapes with said head and a second locking cooperation of shapes with said plate, the member being adapted to provide the first cooperation with the non-circular section of the head and the member does not extend below the surface of the vertebrae.

2. System according to claim 1, wherein the first locking cooperation of shapes includes straddling of said non-circular section head by said member from above.

3. System according to claim 2, wherein the member has two lateral legs delimiting between them a channel with straight edges whose width is slightly greater than the distance between two parallel flats of the head of said pedicular screw.

4. System according to claim 3 wherein the second locking cooperation of shapes includes straddling of said plate by said member from below.

5. System according to claim 4, wherein said member has two lateral columns defining between them a channel with oblique raised edges and in that said plate has lateral bevels adapted to bear against said oblique edges.

6. System according to claim 5, wherein said plate bears only on said oblique edges of said member.

7. System according to claim 1, wherein said member has a core which is generally disk-shaped with a central hole through it through which the threaded end shank of the pedicular screw can be passed.

8. System according to claim 1, wherein the width of the member is substantially equal to that of the plate.

9. System according to claim 1, wherein the system includes a set of pedicular screws and a set of plates having different configurations of holes, with one slightly oblong hole of constant geometry and one or more elongate holes of different lengths.

10. System according to claim 1, wherein the nut bears directly against the top face of the plate.

11. System for osteosynthesis of the spine, including at least two pedicular screws for insertion into vertebrae and a connecting plate adapted to connect the screws together in an essentially rigid manner, each screw having a bone anchor threaded part and a non-circular section head, as well as a threaded end shank adapted to cooperate with a nut, the plate having at least one opening adapted to have the threaded end shank of a screw passed through it and to be trapped between said head and said nut, a locking member being provided for preventing relative angular movement between the head of each pedicular screw and the plate, the locking member including an attached member added between said plate and said head of the pedicular screw and through which the threaded end shank of the latter passes, wherein the attached member provides a first locking cooperation of shapes with said head and a second locking cooperation of shapes with said plate, the attached member being adapted to provide the first cooperation with the non-circular section of the head and wherein said attached member has two lateral columns defining between them a channel with oblique raised edges and in that said plate has lateral bevels adapted to bear against said oblique edges.

12. System according to claim 11, wherein said plate bears only on said oblique edges of said attached member.

13. System according to claim 11, wherein the first locking cooperation of shapes includes straddling of said non-circular section head by said attached member from above.

14. System according to claim 13, wherein the attached member has two lateral legs delimiting between them a channel with straight edges whose width is slightly greater than the distance between two parallel flats of the head of said pedicular screw.

15. System according to claim 14, wherein the second locking cooperation of shapes includes straddling of said plate by said attached member from below.

16. System according to claim 15, wherein said attached member has a core which is generally disk-shaped with a central hole through it through which the threaded end shank of the pedicular screw can be passed.

17. System according to claim 16, wherein the width of the attached member is substantially equal to that of the plate.

18. System according to claim 17, wherein the system includes a set of pedicular screws and a set of plates having different configurations of holes, with one slightly oblong hole of constant geometry and one or more elongate holes of different lengths.

19. System according to claim 18, wherein the nut bears directly against the top face of the plate.

* * * * *